United States Patent
Rydberg et al.

(10) Patent No.: US 6,337,054 B1
(45) Date of Patent: Jan. 8, 2002

(54) METHOD AND APPARATUS FOR REGULATING HEAT FLOW IN AUTOCLAVES

(75) Inventors: Carl-Magnus Rydberg, Halmstad (SE); Arve Tönnesen, Halden (NO)

(73) Assignee: Getinge AB, Getinge (SE)

( * ) Notice: Subject to any disclaimer, the term of this patent is extended or adjusted under 35 U.S.C. 154(b) by 0 days.

(21) Appl. No.: 09/355,263

(22) PCT Filed: Jan. 27, 1997

(86) PCT No.: PCT/SE97/00125
§ 371 Date: Sep. 27, 1999
§ 102(e) Date: Sep. 27, 1999

(87) PCT Pub. No.: WO98/32471
PCT Pub. Date: Jul. 30, 1998

(51) Int. Cl.[7] .................................................. A61L 2/07
(52) U.S. Cl. ...................... 422/295; 422/243; 422/292; 422/109; 422/108; 422/105
(58) Field of Search ................................ 422/109, 295, 422/243, 292, 105, 108; 340/870

(56) References Cited

U.S. PATENT DOCUMENTS

| | | |
|---|---|---|
| 3,908,533 A | 9/1975 | Fagerstrom et al. |
| 4,108,601 A | 8/1978 | Wolff |
| 4,127,384 A | 11/1978 | Fahlvik et al. |
| 4,560,346 A | 12/1985 | Schulz |
| 5,164,161 A * | 11/1992 | Feathers et al. ............ 422/109 |
| 5,426,428 A * | 6/1995 | Binder et al. .......... 340/870.17 |

FOREIGN PATENT DOCUMENTS

| | | |
|---|---|---|
| DE | 3536008 A1 | 4/1987 |
| EP | 0133239 A2 | 2/1985 |
| EP | 0272602 | 6/1988 |

* cited by examiner

Primary Examiner—Robert J. Warden, Sr.
Assistant Examiner—Sean E. Conley
(74) Attorney, Agent, or Firm—Burns, Doane, Swecker & Mathis, L.L.P.

(57) ABSTRACT

The invention relates to a method in autoclaves, the autoclave being divided into imaginary areas, the areas being heated by the feeding of steam into the areas in order to heat goods which have been placed in the autoclave so that it reaches sterilising temperature, whereby the feeding of heat between the areas is controlled. Such control is effected by successive registration of the temperatures in the areas and when the temperatures differ between the areas, the feeding of steam to the area which temporarily has a higher temperature is ceased, and as soon as the temperature in the adjacent area has passed the last mentioned temperature, the feeding of steam to that same area is resumed. In a device for the carrying out of the method, a temperature meter is arranged in each area. These meters are connected to a control unit, which is arranged to register the measured temperatures given by the meters and to control the function of the valves in the steam feeding pipes to the areas according to the method of the invention.

2 Claims, 1 Drawing Sheet

METHOD AND APPARATUS FOR REGULATING HEAT FLOW IN AUTOCLAVES

Figure 1:
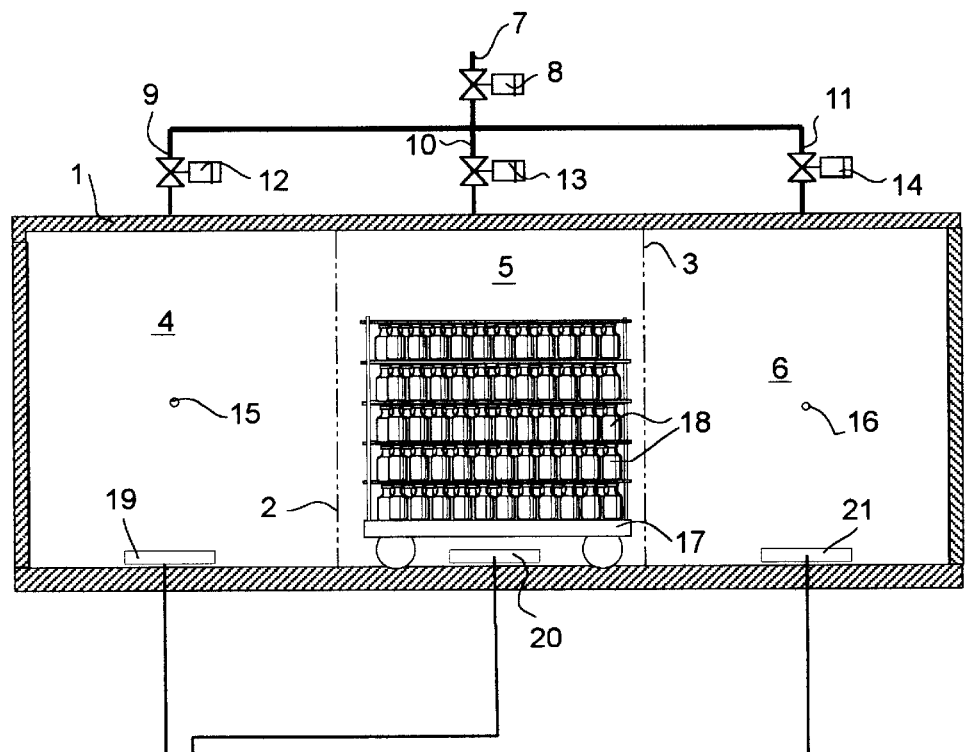

The invention relates to a method and a device in autoclaves, comprising a container which is divided into imaginary areas, which are heated by the feeding of steam into the areas in order to heat goods which have been placed in the autoclave so that said goods reach sterilising temperature.

For a long time, these kinds of autoclaves have been used when sterilising newly manufactured products which have to be sterilised before being put on the market. Infusion solutions, such as glucose or blood plasma, or vitamins and proteins in solid or liquid state are examples of such products.

After completed manufacture of a product of any of the above mentioned kinds, the product is loaded as goods onto carriages, the carriages being placed in one area each in the autoclave, said autoclave will subsequently be closed, and steam will be fed into each area in order to sterilise the goods.

The products are manufactured according to the market demand, usually in very different quantities depending on the product. A problem in this connection is that the demand for a product might be so small that within a certain time one is able to fill one carriage only, whilst the autoclave is dimensioned for several carriages. Disregarding this fact and leaving one or several areas in the autoclave empty during the sterilising process is however, most disadvantageous. Steam which is fed into the empty area/areas will flow to the cool goods on the carriage and consequently the outermost goods will become more rapidly heated than the goods placed in the centre. Said goods may be of a nature that does not allow exposure to too high temperatures during too long periods. This would happen in the above mentioned case where the duration of the sterilising process is determined by a measuring probe which is placed at the centre of the carriage. For thermolabile goods, such as sugar solutions (glucose), the reaching of high temperatures at too early a stage would lead to caramelization, which in turn would lead to the goods having to be discarded. Thus, development of the sterilising process is achieved only when the interplay between heat and time is correct.

Nor is it advisable to choose an alternative arrangement where, after having loaded goods for sterilisation onto a carriage, the sterilisation of a product is postponed until sufficient quantities have been produced to fill the autoclave with carriages containing the same kind of sterilising goods. Several kinds of products are so sensitive that they have to be discarded if they are not sterilised within a few hours of the manufacturing.

By means of the invention, a method, by which the above described problem can be solved has been provided by regulating the feeding of steam and consequently the feeding of heat into the different areas of the autoclave. The method is characterised in that upon registration in one area of a temperature which by a predetermined number of degrees exceeds the simultaneously registered temperature level in another area, preferably the adjacent area, the feeding of steam to the first-mentioned area will be interrupted and upon registration of a temperature in the same area which equals the level of, or is close to the level of said other or adjacent area, steam will again be fed to the first-mentioned area.

The characteristic features of the device for carrying out the method according to the invention are described in the appended claim 2.

Figure 2:
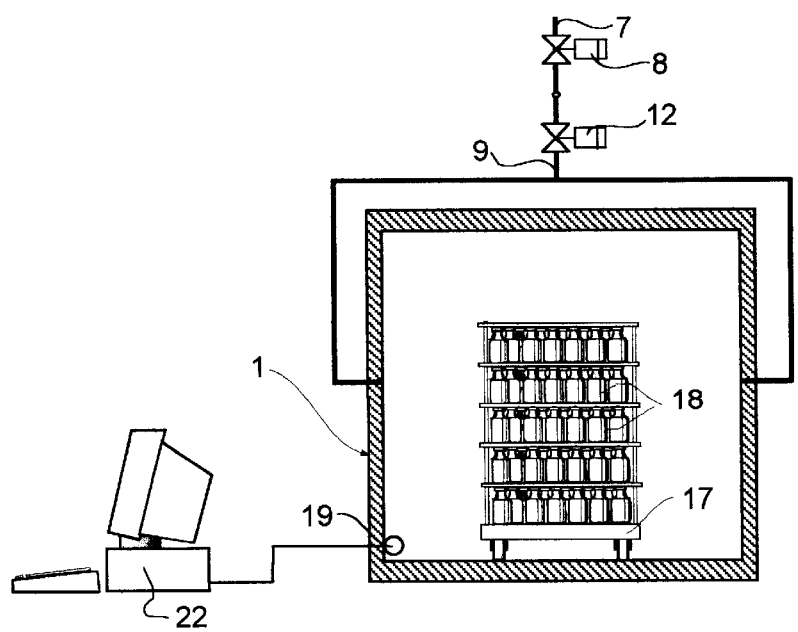

The method and the device according to the invention will be described in closer detail in the following with reference to the accompanying drawing, in which FIG. 1 illustrates a longitudinal sectional view of an autoclave and FIG. 2 illustrates a cross-section of the same autoclave.

The autoclave illustrated comprises a container 1, which has been divided into three imaginary areas 4, 5 and 6 by dash-and-dot lines. From a steam source not illustrated a main pipe 7 feeds steam through a main valve 8 and three branches 9, 10, 11 and closing valves 12, 13 and 14 respectively to the three areas 4, 5 and 6 in the container 1. In the drawing, the charging hole 15 of the pipe 9 in the area 4 and the charging hole 16 of the pipe 11 in the area 6 are the only ones illustrated. In the area 5 is placed a carriage 17 with goods 18 thereon, in the example shown said goods consisting of bottles containing some kind of solution which is to be sterilised.

According to the invention, each area 4, 5, 6 has a temperature meter 19, 20 and 21 respectively. These meters 19, 20, 21 are connected to a control unit 22, which is arranged to register the levels of temperature measured by the meters.

In order to elucidate the invention and its function, an area 5 has been illustrated in the drawing, which area has partly been filled with sterilising goods 18, while the remaining areas 4 and 6 are empty. If traditional technology is used, the steam is fed in equal quantities into all areas 4, 5, 6, making the hot steam in the areas 4 and 6 flow towards the goods 18 which in the initial stage is cool, and primarily heat the outermost bottles on each side. These bottles will thus reach sterilising temperature earlier than the mid-section of the goods 18, where the sensing which decides the length of the sterilising time takes place. The peripheral portions of the goods 18 will thus have too high a temperature during too long a period of time and consequently, if the goods 18 is thermolabile, be destroyed.

According to the invention, the control unit 22 is arranged to control the function of the valves 12, 13, and 14 in such a way that when, in the areas 4 or 6 wherein the temperature rises more quickly, said control unit registers a temperature which reaches a predetermined level, which is, for example 5° C., higher than the temperature simultaneously registered in the area 5, the control unit makes the valve 12 and/or the valve 14 cut off the feeding of steam to the area 4 and/or 6. When a temperature is registered in these areas 4 and 6 equalling that of, or close to the temperature of the mid-area 5, where, meanwhile, the temperature is rising, the control unit 22 is arranged to make the valve 12 and/or the valve 14 to open its corresponding pipe 9, 11 whereby steam will again be fed into the area 4 and/or 6. Due to the regulation by the control unit during the entire development of the sterilising process, the feeding of heat to the sterilising goods 18 will be automatically adjusted in relation to time, thus ensuring that the development of the sterilising process is carried out in a correct way.

The method and the device according to the invention facilitates the entire process. Hence, an operator can arbitrarily place one carriage 17 in each area 4, 5, 6 in the autoclave or in one or two of these areas only. In the case where only one carriage 17 with goods 18 is to be placed in the autoclave the operator need not consider into which area 4, 5, 6 to place this carriage 17, but instead, the operator can arbitrarily place the carriage in any of the areas.

The invention is not limited to the illustrated and described embodiment but can of course be varied in several ways within the scope of the appended claims. Hence, the invention may also be used in an autoclave which is divided into two areas or into a much larger number of areas than illustrated, and into which autoclave several carriages 17 are positioned, while simultaneously, several areas are empty.

What is claimed is:

1. A method for regulating the flow of heat between areas in an autoclave, comprising:

placing goods to be sterilized in a container of the autoclave, the container having a plurality of areas;

heating the container by feeding steam into the areas in order to heat the goods so that the goods reach a sterilizing temperature;

regulating feeding of steam to the container such that, upon registration in a first area of the plurality of areas of a temperature level which exceeds by a predetermined number of degrees a simultaneously registered temperature level in a second area of the plurality of areas, feeding of steam to the first area is interrupted and, upon registration of a temperature level in the first area which substantially equals a temperature level of the second area, steam is fed to the first area.

2. A heat regulating autoclave arrangement, comprising:

a container into which goods to be sterilized are adapted to be placed;

a plurality of pipes connected to the container;

a plurality of valves corresponding to the plurality of pipes, each pipe having a valve, wherein steam is adapted to be delivered to a plurality of different areas of the container through the pipes for heating the goods to a sterilizing temperature;

a plurality of temperature meters arranged in each of the different areas of the container;

a control unit arranged to receive signals from the plurality of temperature meters, to register temperature levels in the different areas measured by the temperature meters, and to control the valves such that, upon registration in a first area of the different areas of a temperature level which exceeds, by a predetermined number of degrees, a temperature level in a second area, a valve on a pipe to the first area is closed to cut off steam to the first area and, upon registration of a temperature level in the first area of substantially the same temperature level of the second area the valve on the pipe to the first area is opened to permit a flow of steam into the first area.

* * * * *